(12) United States Patent
Kondo et al.

(10) Patent No.: US 9,803,213 B2
(45) Date of Patent: Oct. 31, 2017

(54) METHOD FOR IMPARTING ENVIRONMENTAL STRESS RESISTANCE TO PLANTS

(71) Applicants: TOYOTA JIDOSHA KABUSHIKI KAISHA, Toyota-shi, Aichi (JP); OKAYAMA PREFECTURE, Okayama-shi, Okayama (JP)

(72) Inventors: Satoshi Kondo, Toyota (JP); Chikara Ohto, Toyota (JP); Kenichi Ogawa, Kyoto (JP); Kenji Henmi, Kurashiki (JP)

(73) Assignees: TOYOTA JIDOSHA KABUSHIKI KAISHA, Toyota-shi, Aichi-ken (JP); OKAYAMA PREFECTURE, Okayama-shi, Okayama (JP)

( * ) Notice: Subject to any disclaimer, the term of this patent is extended or adjusted under 35 U.S.C. 154(b) by 0 days.

(21) Appl. No.: 14/389,127

(22) PCT Filed: Apr. 17, 2013

(86) PCT No.: PCT/JP2013/061397
§ 371 (c)(1),
(2) Date: Sep. 29, 2014

(87) PCT Pub. No.: WO2013/157580
PCT Pub. Date: Oct. 24, 2013

(65) Prior Publication Data
US 2015/0059020 A1 Feb. 26, 2015

(30) Foreign Application Priority Data
Apr. 18, 2012 (JP) .................. 2012-094931

(51) Int. Cl.
C12N 15/82 (2006.01)
C12N 9/16 (2006.01)
A01H 1/04 (2006.01)

(52) U.S. Cl.
CPC ........... *C12N 15/8273* (2013.01); *A01H 1/04* (2013.01); *C12N 9/16* (2013.01); *C12N 15/8271* (2013.01); *C12Y 301/03048* (2013.01)

(58) Field of Classification Search
None
See application file for complete search history.

(56) References Cited

U.S. PATENT DOCUMENTS

2006/0041961 A1* 2/2006 Abad .................. C07K 14/415
800/289

FOREIGN PATENT DOCUMENTS

CN         102016014 A      4/2011
WO     2009/132057 A1     10/2009

OTHER PUBLICATIONS

Hwang et al (2008 J. Appl. Biol. Chem. 51(2), 50-56, provided by Applicant.*
AtPTP1, 3aD10(361), Proceedings of the 49th conference of the Japanese Society of Plant Physiologists, Mar. 15, 2008, p. 193.
AtPTP1, 1pl07(226), Proceedings of the 50th conference of the Japanese Society of Plant Physiologists, Mar. 16, 2009, p. 166.
Eul-Won Hwang, et al., "Expressing the tyrosine phosphatase (CaTPP1) gene from *Capsicum annuum* in Tobacco enhances cold and drought tolerances", J. Appl. Biol. Chem., 2008, p. 50-56, vol. 51, No. 2.
Eul-Won Hwang, et al., "Expression profiles of hot pepper (*Capsicum annuum*) genes under cold stress conditions", J. Biosci., Dec. 2005, p. 657-667, vol. 30, No. 5.
Xu Qiang, et al., "Molecular characterization of tyrosine-specific protein phosphatase encoded by a stress-responsive gene in Arabidopsis", Plant Cell, May 1998, p. 849-857, vol. 10.
Tim Jacoby. Et al., "Two protein-tyrosine phosphatases inactivate the osmotic stress response pathway in yeast by targeting the mitogen-activated protein kinase Hog1", J. Appl. Biol. Chem., Jul. 11, 1997, p. 17749-17755, vol. 272, No. 28.

* cited by examiner

*Primary Examiner* — Brent Page
(74) *Attorney, Agent, or Firm* — Sughrue Mion, PLLC

(57) ABSTRACT

Environmental stress resistance is imparted to a plant or the environmental stress resistance of a plant is improved. Environmental stress resistance is imparted to a plant by changing the expression level of the tyrosine phosphatase gene (At1g71860).

18 Claims, 8 Drawing Sheets

T: Detection of border region with inserted T-DNA
G: Detection of AtPTP1 gene (Partial)
M: 100 bp DNA Ladder (TAKARA BIO INC)

atptp1-1    atptp1-2    Col

SEQUENCE LISTING

```
<160> NUMBER OF SEQ ID NOS: 15

<210> SEQ ID NO 1
<211> LENGTH: 1023
<212> TYPE: DNA
<213> ORGANISM: Arabidopsis thaliana
<220> FEATURE:
```

```
<221> NAME/KEY: CDS
<222> LOCATION: (1)..(1023)

<400> SEQUENCE: 1 atg gcg acc ggt aaa acc tct tcc gcc gcg aat ctt ttc act ggc tcg      48
Met Ala Thr Gly Lys Thr Ser Ser Ala Ala Asn Leu Phe Thr Gly Ser
1               5                   10                  15 acg cgt ttt gat tta tca tcc gct gat tcg cct cct tca aaa ctc tct      96
Thr Arg Phe Asp Leu Ser Ser Ala Asp Ser Pro Pro Ser Lys Leu Ser
            20                  25                  30 ctc tcc tcc gat cag ctc aac cac tgc cac caa gct ctc ggc gtt ttc     144
Leu Ser Ser Asp Gln Leu Asn His Cys His Gln Ala Leu Gly Val Phe
        35                  40                  45 cgg gga aag atc caa aat cct gac tcg atc gct cat gag ttt acc ggt     192
Arg Gly Lys Ile Gln Asn Pro Asp Ser Ile Ala His Glu Phe Thr Gly
    50                  55                  60 tta cag gct aat agg atg tgg cca tcg gag ctg ctg cta aac agt aca     240
Leu Gln Ala Asn Arg Met Trp Pro Ser Glu Leu Leu Leu Asn Ser Thr
65                  70                  75                  80 gtg gct atg aac agt gtc aat gtt gag aaa aac aga tac agt gat gtt     288
Val Ala Met Asn Ser Val Asn Val Glu Lys Asn Arg Tyr Ser Asp Val
                85                  90                  95 gtt cca ttt gac aag aac agg att gtt ctg aat cca tgt aaa gac tca     336
Val Pro Phe Asp Lys Asn Arg Ile Val Leu Asn Pro Cys Lys Asp Ser
            100                 105                 110 tct gca aaa gga tat gtg aat gca agc tta att aag acg tcg gag tct     384
Ser Ala Lys Gly Tyr Val Asn Ala Ser Leu Ile Lys Thr Ser Glu Ser
        115                 120                 125 gag agt att tct cag ttc ata gct acg caa ggt cct tta cca cac acg     432
Glu Ser Ile Ser Gln Phe Ile Ala Thr Gln Gly Pro Leu Pro His Thr
    130                 135                 140 atg gag gac ttc tgg gag atg gtt att cag cag cat tgc cca atc ata     480
Met Glu Asp Phe Trp Glu Met Val Ile Gln Gln His Cys Pro Ile Ile
145                 150                 155                 160 gtg atg ctc act cga ttg gtt gat aat aat agg act gtt aaa tgc ggg     528
Val Met Leu Thr Arg Leu Val Asp Asn Asn Arg Thr Val Lys Cys Gly
                165                 170                 175 gac tat ttt caa gac gaa gat gga cct aga gaa ttt ggc aac ata tct     576
Asp Tyr Phe Gln Asp Glu Asp Gly Pro Arg Glu Phe Gly Asn Ile Ser
            180                 185                 190 ctt aca aca aag tgg ata aag act act gac act tca ttg atg tta cgg     624
Leu Thr Thr Lys Trp Ile Lys Thr Thr Asp Thr Ser Leu Met Leu Arg
        195                 200                 205 aat ctt gag gtt aac tac aag gag aca gag gat cag ccc atg tcc gtt     672
Asn Leu Glu Val Asn Tyr Lys Glu Thr Glu Asp Gln Pro Met Ser Val
    210                 215                 220 ttg cat att cag tat cca gaa tgg cct gat cat gga gtt ccc aag gat     720
Leu His Ile Gln Tyr Pro Glu Trp Pro Asp His Gly Val Pro Lys Asp
225                 230                 235                 240 aca gtg gct gtc cgt gaa att cta aaa aga cta tat caa gta cca cct     768
Thr Val Ala Val Arg Glu Ile Leu Lys Arg Leu Tyr Gln Val Pro Pro
                245                 250                 255 agt ctc ggc cca atc att gtg cac tgc agt gca ggt ata gga aga act     816
Ser Leu Gly Pro Ile Ile Val His Cys Ser Ala Gly Ile Gly Arg Thr
            260                 265                 270 gga aca tac tgt gcg ata cat aac aca atc caa aga att ctt gct ggc     864
Gly Thr Tyr Cys Ala Ile His Asn Thr Ile Gln Arg Ile Leu Ala Gly
        275                 280                 285 gat atg tct gcg ttg gat ctt gct aaa acc gtg gca cta ttt cgc aag     912
Asp Met Ser Ala Leu Asp Leu Ala Lys Thr Val Ala Leu Phe Arg Lys
```

-continued

```
                    290                 295                 300
caa cgc att ggc atg gtt caa acc atg gat caa tac ttc ttt tgc tac      960
Gln Arg Ile Gly Met Val Gln Thr Met Asp Gln Tyr Phe Phe Cys Tyr
305                 310                 315                 320 aat gct att gtt gat gaa tta gaa gat cta acc gcg ggg aca aat gct     1008
Asn Ala Ile Val Asp Glu Leu Glu Asp Leu Thr Ala Gly Thr Asn Ala
                325                 330                 335 gga acg agt tcc taa                                                 1023
Gly Thr Ser Ser
            340

<210> SEQ ID NO 2
<211> LENGTH: 340
<212> TYPE: PRT
<213> ORGANISM: Arabidopsis thaliana

<400> SEQUENCE: 2

Met Ala Thr Gly Lys Thr Ser Ala Ala Asn Leu Phe Thr Gly Ser
1               5                   10                  15

Thr Arg Phe Asp Leu Ser Ser Ala Asp Ser Pro Ser Lys Leu Ser
                20                  25                  30

Leu Ser Ser Asp Gln Leu Asn His Cys His Gln Ala Leu Gly Val Phe
                35                  40                  45

Arg Gly Lys Ile Gln Asn Pro Asp Ser Ile Ala His Glu Phe Thr Gly
    50                  55                  60

Leu Gln Ala Asn Arg Met Trp Pro Ser Glu Leu Leu Leu Asn Ser Thr
65                  70                  75                  80

Val Ala Met Asn Ser Val Asn Val Glu Lys Asn Arg Tyr Ser Asp Val
                85                  90                  95

Val Pro Phe Asp Lys Asn Arg Ile Val Leu Asn Pro Cys Lys Asp Ser
                100                 105                 110

Ser Ala Lys Gly Tyr Val Asn Ala Ser Leu Ile Lys Thr Ser Glu Ser
            115                 120                 125

Glu Ser Ile Ser Gln Phe Ile Ala Thr Gln Gly Pro Leu Pro His Thr
    130                 135                 140

Met Glu Asp Phe Trp Glu Met Val Ile Gln Gln His Cys Pro Ile Ile
145                 150                 155                 160

Val Met Leu Thr Arg Leu Val Asp Asn Asn Arg Thr Val Lys Cys Gly
                165                 170                 175

Asp Tyr Phe Gln Asp Glu Asp Gly Pro Arg Glu Phe Gly Asn Ile Ser
            180                 185                 190

Leu Thr Thr Lys Trp Ile Lys Thr Thr Asp Thr Ser Leu Met Leu Arg
    195                 200                 205

Asn Leu Glu Val Asn Tyr Lys Gly Thr Glu Asp Gln Pro Met Ser Val
210                 215                 220

Leu His Ile Gln Tyr Pro Glu Trp Pro Asp His Gly Val Pro Lys Asp
225                 230                 235                 240

Thr Val Ala Val Arg Glu Ile Leu Lys Arg Leu Tyr Gln Val Pro Pro
                245                 250                 255

Ser Leu Gly Pro Ile Ile Val His Cys Ser Ala Gly Ile Gly Arg Thr
            260                 265                 270

Gly Thr Tyr Cys Ala Ile His Asn Thr Ile Gln Arg Ile Leu Ala Gly
    275                 280                 285

Asp Met Ser Ala Leu Asp Leu Ala Lys Thr Val Ala Leu Phe Arg Lys
    290                 295                 300
```

```
Gln Arg Ile Gly Met Val Gln Thr Met Asp Gln Tyr Phe Phe Cys Tyr
305                 310                 315                 320

Asn Ala Ile Val Asp Glu Leu Glu Asp Leu Thr Ala Gly Thr Asn Ala
                325                 330                 335

Gly Thr Ser Ser
            340
```

<210> SEQ ID NO 3
<211> LENGTH: 23
<212> TYPE: DNA
<213> ORGANISM: Artificial Sequence
<220> FEATURE:
<223> OTHER INFORMATION: Synthetic DNA

<400> SEQUENCE: 3
tttcgcctgc tggggcaaac cag    23

<210> SEQ ID NO 4
<211> LENGTH: 20
<212> TYPE: DNA
<213> ORGANISM: Artificial Sequence
<220> FEATURE:
<223> OTHER INFORMATION: Synthetic DNA

<400> SEQUENCE: 4
caaccaatcg agtgagcatc    20

<210> SEQ ID NO 5
<211> LENGTH: 20
<212> TYPE: DNA
<213> ORGANISM: Artificial Sequence
<220> FEATURE:
<223> OTHER INFORMATION: Synthetic DNA

<400> SEQUENCE: 5
cagtggctat gaacagtgtc    20

<210> SEQ ID NO 6
<211> LENGTH: 20
<212> TYPE: DNA
<213> ORGANISM: Artificial Sequence
<220> FEATURE:
<223> OTHER INFORMATION: Synthetic DNA

<400> SEQUENCE: 6
acagaggatc agcccatgtc    20

<210> SEQ ID NO 7
<211> LENGTH: 23
<212> TYPE: DNA
<213> ORGANISM: Artificial Sequence
<220> FEATURE:
<223> OTHER INFORMATION: Synthetic DNA

<400> SEQUENCE: 7
ttaggaactc gttccagcat ttg    23

<210> SEQ ID NO 8
<211> LENGTH: 22
<212> TYPE: DNA
<213> ORGANISM: Artificial Sequence
<220> FEATURE:
<223> OTHER INFORMATION: Synthetic DNA

<400> SEQUENCE: 8

```
gtcctttacc acacacgatg ga                                              22
```

<210> SEQ ID NO 9
<211> LENGTH: 18
<212> TYPE: DNA
<213> ORGANISM: Artificial Sequence
<220> FEATURE:
<223> OTHER INFORMATION: Synthetic DNA

<400> SEQUENCE: 9

```
ttgggcaatg ctgctgaa                                                   18
```

<210> SEQ ID NO 10
<211> LENGTH: 21
<212> TYPE: DNA
<213> ORGANISM: Artificial Sequence
<220> FEATURE:
<223> OTHER INFORMATION: Synthetic DNA

<400> SEQUENCE: 10

```
tcctagtaag cgcgagtcat c                                               21
```

<210> SEQ ID NO 11
<211> LENGTH: 20
<212> TYPE: DNA
<213> ORGANISM: Artificial Sequence
<220> FEATURE:
<223> OTHER INFORMATION: Synthetic DNA

<400> SEQUENCE: 11

```
cgaacacttc accggatcat                                                 20
```

<210> SEQ ID NO 12
<211> LENGTH: 26
<212> TYPE: DNA
<213> ORGANISM: Artificial Sequence
<220> FEATURE:
<223> OTHER INFORMATION: Synthetic DNA

<400> SEQUENCE: 12

```
tctagaatgg cgaccggtaa aacctc                                          26
```

<210> SEQ ID NO 13
<211> LENGTH: 26
<212> TYPE: DNA
<213> ORGANISM: Artificial Sequence
<220> FEATURE:
<223> OTHER INFORMATION: Synthetic DNA

<400> SEQUENCE: 13

```
gagctcttag gaactcgttc cagcat                                          26
```

<210> SEQ ID NO 14
<211> LENGTH: 28
<212> TYPE: DNA
<213> ORGANISM: Artificial Sequence
<220> FEATURE:
<223> OTHER INFORMATION: Synthetic DNA

<400> SEQUENCE: 14

```
gactgttaaa tccggggact attttcaa                                        28
```

<210> SEQ ID NO 15
<211> LENGTH: 28
<212> TYPE: DNA
<213> ORGANISM: Artificial Sequence -continued

```
<220> FEATURE:
<223> OTHER INFORMATION: Synthetic DNA

<400> SEQUENCE: 15
aatagtcccc ggatttaaca gtcctatt                                              28
```

METHOD FOR IMPARTING ENVIRONMENTAL STRESS RESISTANCE TO PLANTS

CROSS REFERENCE TO RELATED APPLICATIONS

This application is a National Stage of International Application No. PCT/JP2013/061397 filed Apr. 17, 2013, claiming priority based on Japanese Patent Application No. 2012-094931, filed Apr. 18, 2012, the contents of all of which are incorporated herein by reference in their entirety.

TECHNICAL FIELD

The present invention relates to a method for imparting environmental stress resistance to plants by changing the expression level of a predetermined gene.

BACKGROUND ART

The possibility of plant growth depends on different environmental factors such as temperature, humidity, and concentrations of salts in soil. In some cases, an environment characterized by such factors is suitable for a certain plant but not for other plants. In general, the above factors that would influence plant growth are referred to as environmental stresses. Cases in which a given plant cannot grow or can grow but with difficulty in an environment characterized by certain environmental stresses are explained by noting that the plant lacks environmental stress resistance. On the other hand, the ability of a plant to grow in an environment characterized by certain environmental stresses is explained by noting that such plant has environmental stress resistance.

If environmental stress resistance can be imparted to a plant, it becomes possible to expand the area in which the plant can be cultivated, allowing the effective use of limited ground space. In particular, an energy crop such as sugarcane is used as a raw material for biofuel. Therefore, it is desirable for such energy crop to gain resistance to a variety of environmental stresses. That is to say, if environmental stress resistance can be imparted to such an energy crop, the energy crop can be cultivated in an area in which the crop could not otherwise be cultivated due to the above described environmental factors.

As a technique for imparting environmental stress resistance to plants, for example, Patent Document 1 describes a known method for the overexpression of the *Arabidopsis thaliana* tyrosine phosphatase (PTP) gene (At3g44620). According to Patent Document 1, drought resistance can be imparted to plants by causing the overexpression of the PTP gene. Moreover, Non-patent Document 1 describes that the expression of the *Arabidopsis thaliana*-derived tyrosine phosphatase gene (At1g71860) is induced by high-salt treatment.

PRIOR ART DOCUMENTS

Patent Document

Patent Document 1: WO2009-132057

Non-Patent Document

Non-patent Document 1: Xu Q, Fu H H, Gupta R, Luan S. Molecular characterization of a tyrosine-specific protein phosphatase encoded by a stress-responsive gene in *Arabidopsis*. Plant Cell. 1998 May; 10 (5):849-57.

DISCLOSURE OF THE INVENTION

Problem to be Solved by the Invention

However, in general, even when the fact that a given gene is specifically expressed at a high level under conditions corresponding to environmental stresses is known, it cannot be said that a plant modified to be able to express the gene at a high level can always acquire environmental stress resistance. Therefore, how the *Arabidopsis thaliana*-derived tyrosine phosphatase gene (At1g71860) is involved in plants' environmental stress resistance, or whether the gene is never involved in the same, is completely unknown.

Therefore, in view of the above circumstances, it is an object of the present invention to provide a technique for imparting environmental stress resistance to plants or improving the environmental stress resistance of plants.

Means for Solving the Problem

As a result of intensive studies to attain the above object, the present inventors have discovered a new knowledge such that environmental stress resistance can be imparted to a plant by changing the expression level of the tyrosine phosphatase gene (At1g71860), and thus have completed the present invention.

Specifically, the plants according to the present invention are produced by changing the expression level of the At1g71860 gene or a gene functionally equivalent thereto.

In addition, the method for imparting environmental stress resistance to plants of the present invention comprises changing the expression level of the At1g71860 gene or a gene functionally equivalent thereto. The method for producing plants of the present invention comprises the steps of: preparing plants by changing the expression level of the At1g71860 gene or a gene functionally equivalent thereto; and evaluating environmental stress resistance of the plants and selecting a line with significantly improved environmental stress resistance.

In particular, the above At1g71860 gene and a gene functionally equivalent thereto are preferably genes encoding any one of the following proteins (a) to (c):
(a) a protein comprising the amino acid sequence shown in SEQ ID NO: 2;
(b) a protein comprising an amino acid sequence that has a deletion, a substitution, an addition, or an insertion of one or a plurality of amino acids with respect to the amino acid sequence shown in SEQ ID NO: 2 and has tyrosine phosphatase activity; and
(c) a protein that is encoded by a polynucleotide hybridizing under stringent conditions to a polynucleotide consisting of a nucleotide sequence complementary to the nucleotide sequence shown in SEQ ID NO: 1 and has tyrosine phosphatase activity.

Examples of plants to be subjected to the present invention include dicotyledons such as plants of the family Brassicaceae. Examples of plants of the family Brassicaceae include *Arabidopsis thaliana* and rapeseed. Other examples of plants to be subjected to the present invention include monocotyledons such as plants of the family Gramineae. Examples of plants of the family Gramineae include rice and sugarcane.

Moreover, the phrasing, "changing the expression level of a gene" in the present invention refers to both increasing and decreasing the expression level of the gene, regardless of the degree of increase or decrease.

This description includes part or all of the contents as disclosed in the description and/or drawings of Japanese Patent Application No. 2012-094931, which is a priority document of the present application.

Effect of the Invention

The plant of the present invention has significantly improved resistance to environmental stresses such as salt stress, compared with wild-type plants. Also, the method for imparting environmental stress resistance of the present invention can significantly improve resistance of a target plant to environmental stresses, compared with wild-type plants. Furthermore, according to the method for producing the plant of the present invention, plants having significantly improved resistance to environmental stresses compared with wild-type plants can be produced. Therefore, through application of the present invention, for example, plant cultivation conditions can be greatly relaxed, a production amount can be improved when the plant itself is a product, and cost reduction can be achieved.

MODES FOR CARRYING OUT THE INVENTION

Figure 1:
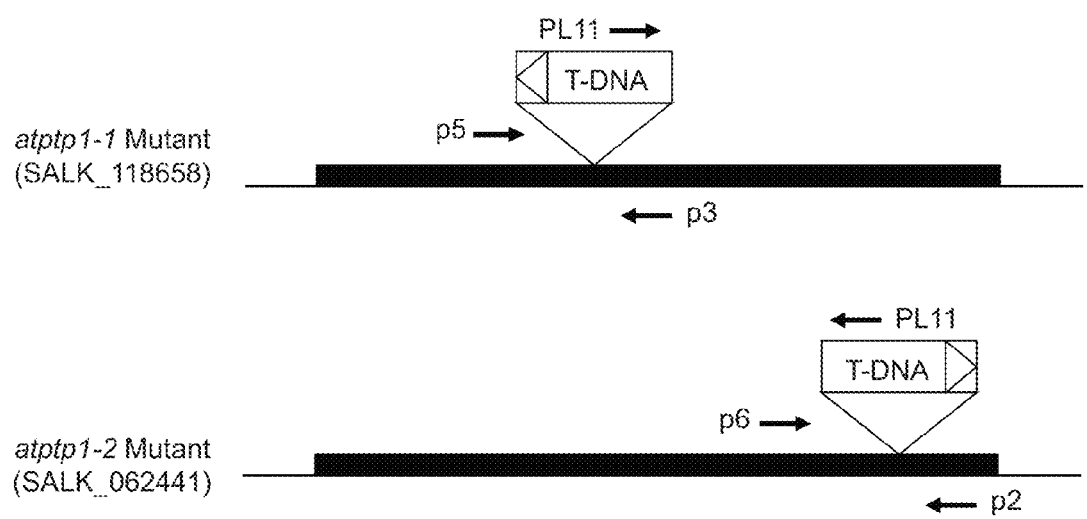
FIG. 1 is a schematic diagram showing the positions of primers designed for confirming the insertion position of T-DNA in atptp1-1 mutant and atptp1-2 mutant.

Hereafter, the present invention is described in detail.

The plant of the present invention is produced by changing the expression level of a specific tyrosine phosphatase gene and thus exhibits environmental stress resistance more significantly improved than that of the wild-type plant. Here, the term "environmental stress" used herein refers to salt stress, high temperature stress, drought stress, and the like. Particularly preferably, the type of environmental stress resistance to be imparted to the plant of the present invention is salt stress resistance. That is, preferably, the plant of the present invention exhibits salt stress resistance more improved than that of the wild-type plant. The improvement of environmental stress resistance such as salt stress resistance indicates that a plant can grow under conditions to which environmental stresses have been applied to make it impossible or difficult for the wild-type plant to grow.

The phrasing, "changing the expression level of a tyrosine phosphatase gene" in the present invention refers to both increasing and decreasing the expression level of the gene. The expression level of a tyrosine phosphatase gene can be changed by performing various modifications as described in detail below. The phrasing "increasing or decreasing the expression level of a tyrosine phosphatase gene" may refer to a statistically significant increase or decrease in the expression level of the gene in a modified plant, compared with the same in an unmodified plant (e.g., wild-type plant). As described above, the phrasing may refer to a statistically significant increase or decrease in the expression level of the gene, regardless of the amount of increase or decrease.

Furthermore, the phrasing, "decreasing the expression level of a tyrosine phosphatase gene" in the present invention is synonymous with suppressing a tyrosine phosphatase gene within a plant. The suppression of the tyrosine phosphatase gene causes a decrease or the loss of specific tyrosine phosphatase activity in a target plant. Here, the phrasing, "suppressing (suppression of) a gene" refers to: deleting the gene from the chromosome; decreasing the expression level of the gene, degrading the transcription product of the gene; decreasing the amount of the gene translated; and degrading or suppressing the expression product (protein) of the gene, for example. In other words, the phrasing "suppressing a specific tyrosine phosphatase gene" refers to introducing a loss-of-function mutant-type mutation into a tyrosine phosphatase gene. More specifically, examples of a technique for suppressing a gene include, namely, a transposon method, a transgene method, posttranscriptional gene silencing, an RNAi method, a nonsense mediated decay (NMD) method, a ribozyme method, an antisense method, miRNA (micro-RNA) method, siRNA (small interfering RNA) method, and an antibody method.

For example, the phrasing "deleting (deletion of) a tyrosine phosphatase gene from the chromosome" refers to, but is not particularly limited to, deleting the expression control region and/or the coding region of the relevant gene from the chromosome. Methods for deleting a tyrosine phosphatase gene from the chromosome are not particularly limited and deletion can be adequately performed according to a standard method.

Moreover, siRNA that suppresses a tyrosine phosphatase gene is mRNA (that is, mRNA that is encoded by the gene) corresponding to the tyrosine phosphatase gene or small double-stranded RNA containing a sequence complementary to the selective spliced mRNA, wherein the mRNA or its selective splicing-type mRNA is selectively processed via the formation of an RNA-nuclease complex (RNA induced silencing complex or RISC).

Furthermore, siRNA may be induced from its precursor, short hairpin RNA (shRNA), via processing by a dicer that is intracellular RNase. shRNA is double-stranded RNA having a loop between the sense strand sequence of siRNA and the antisense strand sequence, and preferably contains an overhang consisting of 1 to 6, and preferably 2 to 4 polyU on the 3' end. shRNA is processed into siRNA by a dicer belonging to the RNaseIII family, single-stranded siRNA is formed, and then its sense strand RNA forms a complex (RISC) with RNaseH, so as to cleave target mRNA having a sequence complementary to the siRNA sequence, thereby suppressing gene expression. When siRNA corresponding to a tyrosine phosphatase gene is introduced into a target plant, direct injection of siRNA or the use of a vector capable of expressing siRNA is preferred.

Specifically, an expression vector containing a DNA sequence encoding the above siRNA or its precursor under regulation of a promoter can be used. An example of an expression vector is a hairpin-type vector. This vector contains DNA encoding hairpin-type RNA in which the above sense strand RNA sequence and the above antisense strand RNA sequence are covalently bound via a single-stranded loop sequence. Here the DNA is a vector whereby the hairpin-type RNA is formed by intracellular transcription, and then it is processed by a dicer to form the above siRNA. Four (4) or 5 poly T sequences each consisting of 1 to 6, and preferably 1 to 5 T, are ligated to the 3' end of hairpin-type DNA encoding siRNA, as transcriptional stop signal sequences or for overhang. shRNA as an siRNA precursor that is transcribed from vector DNA desirably has an overhang consisting of 2 to 4 U at the 3' end of its antisense strand. Due to the presence of the overhang, sense strand RNA and antisense strand RNA can have enhanced stability against degradation by nuclease. An endogenous dicer plays a role in conversion of long chain dsRNA and precursor micro RNA (miRNA) into siRNA and mature miRNA, respectively.

A plasmid vector may generally contain, in addition to a DNA sequence encoding the above siRNA and a promoter, a drug resistance gene (e.g., a neomycin resistance gene, an ampicillin resistance gene, a puromycin resistance gene, and a hygromycin resistance gene), a transcriptional stop sequence, a unique restriction site or multiple cloning sites, a replication origin, and the like.

Moreover, an antisense nucleic acid suppressing a tyrosine phosphatase gene is either RNA or DNA containing a mRNA sequence corresponding to the tyrosine phosphatase gene or a sequence complementary to a partial sequence thereof. The above partial sequence may comprise a sequence of about continuous 30 or more, 50 or more, 70 or more, 100 or more, 150 or more, 200 or more, or 250 or more nucleotides to less than the full length of the tyrosine phosphatase gene or its mRNA sequence thereof.

Examples of nucleotides of an antisense nucleic acid include, in addition to natural nucleotides, modified nucleotides having halogen (fluorine, chlorine, bromine or iodine) or a group such as a methyl, carboxymethyl, or thio group. Antisense nucleic acid can be synthesized using a known DNA/RNA synthesis technique or a known DNA recombination technique. When an antisense nucleic acid is synthesized by a DNA recombination technique, a polymerase chain reaction (PCR) is performed using vector DNA containing the nucleotide sequence of a tyrosine phosphatase gene as a template, and primers flanking a sequence to be amplified, so as to amplify the target sequence. Cloning into a vector is performed as necessary, so that antisense DNA can be generated. Alternatively, DNA having the thus amplified target sequence is inserted into a vector, the vector is introduced into eukaryotic or prokaryotic cells, and thus antisense RNA can be obtained using the transcription system thereof.

The transcription or translation of the antisense nucleic acid of the present invention can be inhibited or suppressed by binding it to a tyrosine phosphatase gene or the corresponding mRNA, regardless of DNA or RNA. Its antisense nucleic acid thereof can also be introduced into a target plant by causing an appropriate vector to carry the antisense nucleic acid in a manner similar to that for the above siRNA.

Furthermore a ribozyme that suppresses a tyrosine phosphatase gene is RNA having catalytic activity and activity of cleaving mRNA corresponding to a target tyrosine phosphatase gene. This cleavage inhibits or suppresses the expression of the tyrosine phosphatase gene. A target sequence that can be cleaved by a ribozyme is generally known to be NUX (N=A,G,C,U; X=A,C,U), such as a sequence containing a GUC triplet. An example of a ribozyme is a hammerhead-type ribozyme. Hammerhead-type ribozyme may contain a nucleotide sequence composing a sensor site, a nucleotide sequence containing a region capable of forming a cavity for stably capturing $Mg^{2+}$ ion only when RNA binds to a sensor site, and a nucleotide sequence containing a region complementary to a sequence in the periphery of the cleavage site of target RNA. The ribozyme of the present invention can be similarly introduced into a target plant by causing an appropriate vector to carry the ribozyme.

Furthermore, the term "antibody that suppresses a tyrosine phosphatase gene" refers to an antibody or a functional fragment thereof, which inhibits or suppresses a tyrosine phosphatase encoded by the tyrosine phosphatase gene. Examples of an antibody against tyrosine phosphatase include monoclonal antibodies, antibodies produced by recombination, chimeric antibodies, single-stranded antibodies, bispecific antibodies, and synthetic antibodies. Examples of functional fragments of the antibodies include, Fab fragment, F(ab')2 fragment, and scFv. In addition, antibody classes and subclasses may be of any type. Examples of an antibody class include IgG, IgM, IgE, IgD, and IgA. Examples of an antibody subclass include IgG1, IgG2, IgG3, IgG4, IgA1, and IgA2. An antibody may also be derivatized by pegylation, acetylation, glycosylation, amidation, or the like.

Meanwhile, the phrasing, "increasing the expression level of a tyrosine phosphatase gene" in the present invention is synonymous with enhancing the activity of tyrosine phosphatase encoded by the tyrosine phosphatase gene within a plant. Examples of a principle of increasing the expression level of a tyrosine phosphatase gene include performing introduction so as to enable the expression of the gene, increasing the amount of the gene transcribed, increasing the amount of the gene translated, and suppressing the degradation of the gene expression product (protein) of the gene. More specifically, examples of a technique for increasing gene expression include a method that involves introducing a tyrosine phosphatase gene located downstream of a promoter into a plant, and a method that involves modifying the expression control region of an endogenous tyrosine phosphatase gene.

Here, a tyrosine phosphatase gene may be introduced by incorporating the gene into a chromosome, or causing an expression vector to carry the gene. At this time, for stable expression of the introduced gene, the gene is preferably introduced into a chromosome so that the expression is enhanced by a promoter for constant expression.

Furthermore, the term "expression control region" refers to a promoter region to which RNA polymerase binds and regions to which other transcription factors bind. An example of the modification of a transcription control region is modification by which a promoter region among endogenous transcription control regions is substituted with a promoter region that enables a higher expression level, for example.

An expression vector is constructed to contain a promoter that enables expression within a plant and the above described tyrosine phosphatase gene. As a vector serving as a mother body for an expression vector, various conventionally known vectors can be used. For example, plasmids, phages, cosmids, or the like can be used and such vector can be appropriately selected depending on plant cells into which it is introduced and introduction methods. Specific examples of such vector include pBR322, pBR325, pUC19, pUC119, pBluescript, pBluescriptSK, and pBI vectors. Particularly, when a method for introduction of a vector into a plant uses *Agrobacterium*, a pBI binary vector is preferably used. Specific examples of such pBI binary vector include pBIG, pBIN19, pBI101, pBI121, and pBI221.

A promoter to be used herein is not particularly limited, as long as it enables expression of a tyrosine phosphatase gene within a plant. Any known promoter can be appropriately used. Examples of such promoter include a cauliflower mosaic virus 35S promoter (CaMV35S), various actin gene promoters, various ubiquitin gene promoters, a nopaline synthase gene promoter, a tobacco PR1a gene promoter, a ribulose 1,5-bisphosphate carboxylase-oxygenase small subunit gene promoter, and a napin gene promoter. Of these, a cauliflower mosaic virus 35S promoter, an actin gene promoter, or an ubiquitin gene promoter can be more preferably used. The use of each of the above promoters enables constant strong expression of the tyrosine phosphatase gene introduced into plant cells.

Also, a promoter having functions of causing site-specific expression in a plant can also be used herein. As such promoter, any conventionally known promoter can be used. A tyrosine phosphatase gene can be site-specifically expressed using such promoter.

In addition, an expression vector may further contain other DNA segments in addition to a promoter and the tyrosine phosphatase gene. Such other DNA segments are not particularly limited and examples thereof include a terminator, a selection marker, an enhancer, and a nucleotide sequence for enhancing translation efficiency. Also, the above recombinant expression vector may further have a T-DNA region. A T-DNA region can enhance efficiency for gene introduction particularly when the above recombinant expression vector is introduced into a plant using *Agrobacterium*.

A transcription terminator is not particularly limited, as long as it has functions as a transcription termination site and may be any known transcription terminator. For example, specifically, a transcription termination region (Nos terminator) of a nopaline synthase gene, a transcription termination region (CaMV35S terminator) of cauliflower mosaic virus 35S, or the like can be preferably used. Of them, the Nos terminator can be more preferably used. In the case of the above recombinant vector, a phenomenon such that an unnecessarily long transcript is synthesized and that a strong promoter decreases the number of copies of a transcript after introduction into plant cells can be prevented by positioning a transcription terminator at an appropriate position.

As a transformant selection marker, a drug resistance gene can be used, for example. Specific examples of such drug resistance gene include drug resistance genes against hygromycin, bleomycin, kanamycin, gentamicin, chloramphenicol, and the like. Transformed plants can be easily selected by selecting plants that can grow in medium containing the above antibiotics.

An example of a nucleotide sequence for increasing translation efficiency is an omega sequence from tobacco mosaic virus. This omega sequence is positioned in an untranslated region (5'UTR) of a promoter, so that the translation efficiency of the fusion gene can be increased. As such, the recombinant expression vector may contain various DNA segments depending on purposes.

A method for constructing a recombinant expression vector is not particularly limited. To an appropriately selected vector serving as a mother body, the above promoter and a tyrosine phosphatase gene, and if necessary, the above other DNA segments may be introduced in a predetermined order. For example, a tyrosine phosphatase gene and a promoter (and, if necessary, a transcription terminator or the like) are linked to construct an expression cassette and then the cassette may be introduced into a vector. In construction of an expression cassette, for example, cleavage sites of each DNA segment are prepared to have protruding ends complementary to each other and then performing a reaction with a ligation enzyme, making it possible to specify the order of the DNA segments. In addition, when an expression cassette contains a terminator, DNA segments may be positioned in the following order from upstream: a promoter, the tyrosine phosphatase gene, and a terminator. Also, reagents for construction of an expression vector (that is, types of restriction enzymes, ligation enzymes, and the like) are also not particularly limited. Hence, commercially available reagents can be appropriately selected and used.

Also, a method for amplifying (a method for producing) the above expression vector is not particularly limited and conventionally known amplification methods can be used herein. In general, such expression vector may be amplified within *Escherichia coli* as a host. At this time, preferred types of *Escherichia coli* may be selected depending on the types of vector.

The above-described expression vector is introduced into a target plant by a general transformation method. A method for introducing an expression vector into plant cells (transformation method) is not particularly limited. Conventionally known appropriate introduction methods can be employed depending on plant cells. Specifically, a method using *Agrobacterium* or a method that involves direct introduction into plant cells can be employed, for example. As a method using *Agrobacterium*, a method described in Bechtold, E., Ellis, J. and Pelletier, G. (1993) In Planta *Agrobacterium*-mediated gene transfer by infiltration of adult *Arabidopsis* plants. C. R. Acad. Sci. Paris Sci. Vie, 316, 1194-1199, or a method described in Zyprian E, Kado Cl, *Agrobacterium*-mediated plant transformation by novel mini-T vectors in conjunction with a high-copy vir region helper plasmid, Plant Molecular Biology, 1990, 15(2), 245-256 can be employed, for example.

As a method for directly introducing an expression vector into plant cells, microinjection, electroporation, a polyethylene glycol method, a particle gun method, protoplast fusion, a calcium phosphate method, or the like can be employed.

Also, when a method for directly introducing DNA into plant cells is employed, DNA that can be sufficiently used herein contains transcriptional units required for the expression of a target gene, such as a promoter and a transcription terminator, and a target gene. Vector functions are not essential in such case. Moreover, a DNA that contains a protein coding region alone of a target gene having no transcriptional unit may be used herein, as long as it is integrated into a host's transcriptional unit and then the target gene can be expressed.

Examples of plant cells, into which the above expression vector or an expression cassette instead of an expression vector, containing a target gene, is introduced, include cells of each tissue of plant organs such as flowers, leaves, and roots, calluses, and suspension-cultured cells. At this time, an appropriate expression vector may be constructed according to the types of plant to be produced or a versatile expression vector may be constructed in advance and then introduced into plant cells.

As described above, tyrosine phosphatase activity within a target plant is changed by changing (increasing or decreasing) the expression level of a tyrosine phosphatase gene within the target plant. Accordingly, the plant can acquire environmental stress resistance such as resistance to high-salt concentrations.

<Tyrosine Phosphatase Gene>

In the present invention, a tyrosine phosphatase gene, the expression level of which is changed, is the gene specified with At1g71860 (abbreviated as At1g71860 gene) or a gene evaluated to be functionally equivalent or identical to the At1g71860 gene. A gene group that is evaluated to be functionally equivalent or identical to the At1g71860 gene can be searched for and identified using SALAD Database, for example.

As examples, the nucleotide sequence of the coding region of the At1g71860 gene is shown in SEQ ID NO: 1, the amino acid sequence of the protein encoded by the At1g71860 gene is shown in SEQ ID NO: 2. The above functionally equivalent gene is not particularly limited, and can be specified by searching databases containing gene sequences of various organisms. Specifically, the DDBJ/EMBL/GenBank International Nucleotide Sequence Databases and SWISS-PROT database are searched using the nucleotide sequence shown in SEQ ID NO: 1 or the amino acid sequence shown in SEQ ID NO: 2 as a query sequence, for example, and thus such a functionally equivalent gene can be easily searched for and identified from known databases.

In addition, in the present invention, such a tyrosine phosphatase gene, the expression level of which is changed, is not limited to the above-described gene specified by the nucleotide sequence shown in SEQ ID NO: 1 and the amino acid sequence shown in SEQ ID NO: 2. Specifically, such a tyrosine phosphatase gene, the expression level of which is changed, may encode a protein that contains an amino acid sequence having a deletion, a substitution, an addition, or an insertion of 1 or a plurality of amino acid sequences with respect to the amino acid sequence shown in SEQ ID NO: 2, and, has tyrosine phosphatase activity. Here, the term, "a plurality of amino acids" refers to 1 to 20, preferably 1 to 10, more preferably 1 to 7, further preferably 1 to 5, and particularly preferably 1 to 3 amino acids, for example. In addition, amino acid deletion, substitution, or addition can be performed by modifying the nucleotide sequence of the above tyrosine phosphatase gene by a technique known in the art. Mutation can be introduced into a nucleotide sequence by a known technique such as Kunkel method or Gapped duplex method or a method according thereto. For example, a mutation is introduced with a mutagenesis kit based on site-directed mutagenesis (e.g., Mutant-K or Mutant-G (both are trade names of TAKARA Bio)) or the like, or a LA PCR in vitro Mutagenesis series kit (trade name, TAKARA Bio). Also, a mutagenesis method may be: a method using a chemical mutation agent represented by EMS (ethyl methanesulfonate), 5-bromouracil, 2-aminopurine, hydroxylamine, N-methyl-N'-nitro-N-nitro soguanidine, or other carcinogenic compounds; or a method that involves radiation treatment or ultraviolet [UV] treatment typically using X-rays, alpha rays, beta rays, gamma rays, an ion beam, or the like.

Also, a tyrosine phosphatase gene, the expression level of which is changed, may be a gene homologous to the At1g71860 gene specified with the nucleotide sequence shown in SEQ ID NO: 1 and the amino acid sequence shown in SEQ ID NO: 2. Here, the term "homologous gene" generally refers to a gene that has evolutionarily branched off from a common ancestor gene, including a homologous gene of 2 types of species (ortholog), and a homologous gene generated by overlapping branching that takes place within the same species (paralog). In other words, the above term "functionally equivalent gene" refers to a homologous gene such as an ortholog or a paralog. Furthermore, the above term "functionally equivalent gene" may also refer to a gene that does not evolve from a common gene, but simply has analogous functions.

Furthermore, a tyrosine phosphatase gene, the expression level of which is changed, may also be a gene encoding a protein that has an amino acid sequence having 70% or more, preferably 80% or more, more preferably 90% or more, and most preferably 95% or more similarity or identity with the amino acid sequence shown in SEQ ID NO: 2, and, has tyrosine phosphatase activity. Here, the value of similarity refers to a value that can be found based on default setting using a computer mounted with a BLAST (Basic Local Alignment Search Tool) program and a database containing gene sequence information.

Furthermore, a tyrosine phosphatase gene, the expression level of which is changed, may also be a gene comprising a polynucleotide that hybridizes under stringent conditions to at least a part of or the entire polynucleotide consisting of the nucleotide sequence shown in SEQ ID NO: 1, and, encoding a protein having tyrosine phosphatase activity. Here, the term "stringent conditions" refers to conditions under which namely a specific hybrid is formed, but a non-specific hybrid is never formed. For example, such conditions comprise hybridization at 45° C. with 6×SSC (sodium chloride/sodium citrate), followed by washing at 50° C. to 65° C. with 0.2-1×SSC and 0.1% SDS. Alternatively, such conditions comprise hybridization at 65° C. to 70° C. with 1×SSC, followed by washing at 65° C. to 70° C. with 0.3×SSC. Hybridization can be performed by a conventionally known method such as a method described in J. Sambrook et al. Molecular Cloning, A Laboratory Manual, 2nd Ed., Cold Spring Harbor Laboratory (1989).

In particular, when the expression level of a tyrosine phosphatase gene is increased, a mutant tyrosine phosphatase gene is preferably modified to be able to maintain the activity under oxidizing conditions. Examples of such oxidizing conditions include conditions involving the presence of oxidized glutathione or hydrogen peroxide. These oxidized glutathione and hydrogen peroxide oxidize and inactivate tyrosine phosphatase. Here, the term "mutant tyrosine phosphatase gene" refers to a gene encoding tyrosine phosphatase having low sensitivity to oxidized glutathione or hydrogen peroxide.

An example of a mutant tyrosine phosphatase gene is a gene encoding tyrosine phosphatase that has low sensitivity to oxidized glutathione or hydrogen peroxide as a result of substitution of the $175^{th}$ cysteine residue with another amino acid in the amino acid sequence shown in SEQ ID NO: 2. Examples of an amino acid to be substituted with the $175^{th}$ cysteine residue are not particularly limited, as long as they can lower the sensitivity to oxidized glutathione or hydrogen peroxide, and include serine. Specifically, tyrosine phosphatase prepared by substitution of the $175^{th}$ cysteine with serine in the amino acid sequence shown in SEQ ID NO: 2, acquires properties such as its low sensitivity to oxidized glutathione or hydrogen peroxide.

As described above, the expression level of a tyrosine phosphatase gene can be increased by introduction of such a mutant tyrosine phosphatase gene modified to be able to maintain its activity under oxidizing conditions. Introduction of such a mutant tyrosine phosphatase gene modified to be able to maintain its activity under oxidizing conditions can improve environmental stress resistance to a degree higher than that of the introduction of a wild-type tyrosine phosphatase gene. In other words, when a mutant tyrosine phosphatase gene modified to be able to maintain its activity under oxidizing conditions is used, even higher effect of improving environmental stress resistance than that of the use of a wild-type tyrosine phosphatase gene can be expected, although the degree of increasing the expression level is low.

Plants to be subjected to the above-described changing of the expression level of a specific tyrosine phosphatase gene, in other words, plants which are subjected to improvement of environmental stress resistance, are not particularly limited. Specifically, changing of the expression level of the above tyrosine phosphatase gene can be expected to have effects of improving the environmental stress resistance of all plants. Examples of target plants include, but are not limited to, dicotyledons and monocotyledons, such as plants (see below) belonging to the families Brassicaceae, Gramineae, Solanaceae, Leguminosae, Salicaceae, and the like.

Family Brassicaceae: *Arabidopsis thaliana*, rapeseed (*Brassica rapa, Brassica napus, Brassica campestris*), cabbage (*Brassica oleracea* var. *capitata*), napa (*Brassica rapa* var. *pekinensis*), ging-geng-cai (*Brassica rapa* var. *chinensis*), turnip (*Brassica rapa* var. *rapa*), turnip greens (*Brassica rapa* var. *hakabura*), potherb mustard (*Brassica rapa* var. *lancinifolia*), komatsuna (*Brassica rapa* var. *peruviridis*), pak choi (*Brassica rapa* var. *chinensis*), daikon (*Raphanus sativus*), Japanese horseradish (*Wasabia japonica*), and the like.

Family Solanaceae: tobacco (*Nicotiana tabacum*), eggplant (*Solanum melongena*), potato (*Solaneum tuberosum*), tomato (*Lycopersicon lycopersicum*), chile pepper (*Capsicum annuum*), petunia, and the like.

Family Leguminosae: soy (*Glycine max*), pea (*Pisum sativum*), broad bean (*Vicia faba*), Wisteria (*Wisteria floribunda*), peanuts (*Arachis hypogaea*), bird's foot trefoil (*Lotus corniculatus* var. *japonicus*), common bean (*Phaseolus vulgaris*), azuki bean (*Vigna angularis*), Acacia, and the like.

Family Asteraceae: florists' daisy (*Chrysanthemum morifolium*), sunflower (*Helianthus annuus*), and the like.

Family Arecaceae: oil palm (*Elaeis guineensis, Elaeis oleifera*), coconut (*Cocos nucifera*), date palm (*Phoenix dactylifera*), copernicia, and the like.

Family Anacardiaceae: wax tree (*Rhus succedanea*), cashew nut (*Anacardium occidentale*), lacquer tree (*Toxicodendron vernicifluum*), mango (*Mangifera indica*), pistachio (*Pistacia vera*), and the like.

Family Cucurbitaceae: pumpkin (*Cucurbita maxima, Cucurbita moschata, Cucurbita pepo*), cucumber (*Cucumis sativus*), snake gourd (*Trichosanthes cucumeroides*), gourd (*Lagenaria siceraria* var. *gourda*), and the like.

Family Rosaceae: almond (*Amygdalus communis*), rose (*Rosa*), strawberry (*Fragaria*), cherry (*Prunus*), apple (*Malus pumila* var. *domestica*), and the like.

Family Caryophyllaceae: carnation (*Dianthus caryophyllus*) and the like.

Family Salicaceae: poplar (*Populus trichocarpa, Populus nigra*, or *Populus tremula*) and the like.

Family Gramineae: corn (*Zea mays*), rice (*Oryza sativa*), barley (*Hordeum vulgare*), wheat (*Triticum aestivum*), bamboo (*Phyllostachys*), sugarcane (*Saccharum officinarum*), napier grass (*Pennisetum pupureum*), erianthus (*Erianthus ravenae*), miscanthus (Japanese silver grass) (*Miscanthus virgatum*), sorghum (*Sorghum*) and switchgrass (*Panicum*), and the like.

Family Liliaceae: tulip (*Tulipa*), lily (*Lilium*), and the like.

Of these examples, energy crops such as sugarcane, corn, rapeseed, and sunflower, which can serve as raw materials for biofuel, may be preferable targets. It is possible to significantly extend cultivation areas and cultivation conditions for a relevant energy crop by improving the environmental stress resistance of the energy crop. Specifically, it becomes possible to cultivate energy crops even in soil or under the influence of environmental factors (e.g., average temperature, concentration of salt in soil, etc.) in which wild-type plants cannot be cultivated. Accordingly, the costs of biofuels such as bioethanol, biodiesel, biomethanol, bio-DME, bioGTL (BTL), and biobutanol can be reduced.

<Other Steps and Methods>

After changing (modification) the expression level of a tyrosine phosphatase gene as described above, a step of selecting plants with a proper trait can be performed by a conventionally known method. Such selection method is not particularly limited. For example, after the growth of modified plants, plants themselves, or arbitrary organs and tissues thereof having significantly improved environmental stress resistance may be selected.

Also, progeny plants can be obtained from the thus obtained plants according to a conventional method. Plants retaining a trait in which the expression level of the tyrosine phosphatase gene has been changed are selected based on the environmental stress resistance. Therefore, a stable plant line capable of exhibiting improved environmental stress resistance because of having the above trait can be produced. Also, plant cells or reproductive materials, such as seeds, fruits, stocks, calluses, tubers, cut ears, or lumps, may be obtained from the resulting plant or a progeny plant thereof. A stable plant line capable of exhibiting improved environmental stress resistance because of having the above trait can be mass-produced therefrom based on such materials.

In addition, the plants in the present invention may include a matter comprising at least any one of an adult plant, plant cells, plant tissue, callus, and seeds. That is, according to the present invention, any matter in a state that allows it to eventually grow to become a plant can be regarded as a plant. In addition, the above plant cells include plant cells in various forms. Examples of such plant cells include suspension-cultured cells, protoplasts, and leaf sections. As a result of proliferation/differentiation of such plant cells, a plant can be obtained. In addition, a plant can be reproduced from plant cells by a conventionally known method depending on the types of plant cells.

EXAMPLES

Hereafter, the present invention is described in greater detail with reference to the examples, although the technical scope of the present invention is not limited to the examples.

Example 1

(1) Selection of *Arabidopsis thaliana* Tyrosine Phosphatase (PTP) Gene

In this example, the gene specified with AGI code: At1g71860 was selected as an *Arabidopsis thaliana* tyrosine phosphatase gene. In addition, At1g71860 is known as a gene characterized by the expression which is enhanced by high-salt concentration treatment, as described in Plant Cell, 10, 849-857, 1998. In this example, a mutant characterized by the suppression of the At1g71860 gene was examined for the possibility of its growth under high-salt concentration conditions.

In addition, the nucleotide sequence of the coding region of the At1g71860 gene is shown in SEQ ID NO: 1, and the amino acid sequence of tyrosine phosphatase that is encoded by the gene is shown in SEQ ID NO: 2.

(2) *Arabidopsis thaliana* T-DNA Tag Line

SALK_118658 and SALK_062441 obtained from the Nottingham *Arabidopsis* Stock Centre (http://nasc.nott.ac.uk/) were used as *Arabidopsis thaliana* T-DNA insertion mutants in which T-DNA had been inserted into the selected At1g71860 gene.

(3) Confirmation of T-DNA Insertion Position and Homo Line

SALK_118658 contained T-DNA inserted into the 4th exon of the At1g71860 gene. SALK_062441 contained T-DNA inserted into the 7th intron of the same. They were named atptp1-1 mutant and atptp1-2 mutant, respectively. Genomic DNA was extracted from the atptp1-1 mutant, the atptp1-2 mutant, and wild-type *Arabidopsis thaliana* (Col) plants.

As primers for detection of the border region into which T-DNA had been inserted in the atptp1-1 mutant, 5'-TTTCGCCTGCTGGGGCAAACCAG-3' (PL11: SEQ ID NO: 3) and 5'-CAACCAATCGAGTGAGCATC-3' (p3: SEQ ID NO: 4) were used. As primers for detection of the At1g71860 gene, 5'-CAGTGGCTATGAACAGTGTC-3' (p5: SEQ ID NO: 5) and p3 were used (FIG. 1). As primers for detection of the border region into which T-DNA had been inserted in the atptp1-2 mutant, 5'-ACAGAGGATCAGCCCATGTC-3' (p6: SEQ ID NO: 6) and PL11 were used. As primers for detection of the At1g71860 gene, p6 and 5'-TTAGGAACTCGTTCCAGCATTTG-3' (p2: SEQ ID NO: 7) were used (FIG. 1). As a control, PCR was also performed for Col with the above primer sets. With any primer set, PCR was always performed under conditions comprising 1 cycle of 94° C. (3 minutes), followed by 25 cycles of 94° C. (30 seconds), 58° C. (1 minute) and 72° C. (1 minute).

Figure 2:
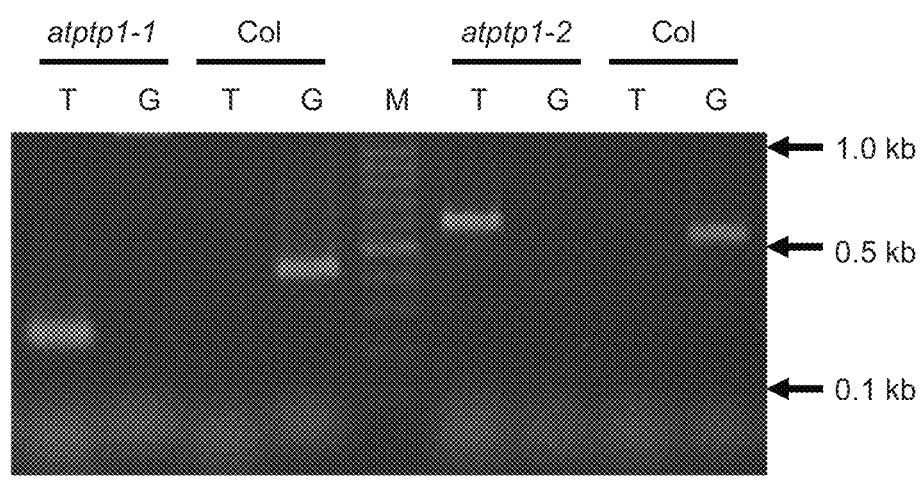
FIG. 2 is an electrophoretic image showing fragments amplified by PCR.

Whereas the border regions into which T-DNA had been inserted were amplified for all mutants, no At1g71860 gene was amplified (the size of the inserted gene was as large as 5 kb or more, so that it was not detectable under such conditions). Normal amplification of the At1g71860 gene was confirmed for Col. Homozygous T-DNA insertion into the At1g71860 gene in these mutants was determined based on these band patterns (FIG. 2).

(4) Comparison of Col and Atptp1 Mutant for the Expression Level of the At1g71860 Gene Total RNA was extracted from all aerial parts of plants grown for 14 days on agar media (½MS, Wako Pure Chemical Industries, Ltd., Murashige and Skoog Plant Salt Mixture), pH 5.7, sucrose concentration 1%, agar 0.7%). cDNA was prepared from 1 µg of the total RNA using an RT-QuantiTect Reverse Transcription kit (Qiagen). After 4-fold dilution for detection of the PLANTSAt1g71860 gene and 1000-fold dilution for detection of 18S rRNA (AGI code: At3g41768.1), the resultants were subjected to Real-Time PCR (Applied Biosystems, Applied Biosystems 7500 Real-Time PCR System). Each reaction solution for detection of the expression of a gene was prepared to a total volume of 24 µl containing 2 µl of diluted cDNA, 1 µl each of 20 µM Forward and Reverse primers, and 12 µl of Power SYBR Green Master Mix (Applied Biosystems). As primers for the At1g71860 gene, 5'-GTCCTTTACCACACAC-GATGGA-3' (SEQ ID NO: 8) and 5'-TTGGGCAATGCT-GCTGAA-3' (SEQ ID NO: 9) were used. As primers for 18S rRNA, 5'-TCCTAGTAAGCGCGAGTCATC-3' (SEQ ID NO: 10) and 5'-CGAACACTTCACCGGATCAT-3' (SEQ ID NO: 11) were used. PCR was performed under conditions comprising 1 cycle of 50° C. (2 minutes) and 95° C. (10 minutes) followed by 40 cycles of 95° C. (15 seconds) and 60° C. (1 minute).

Figure 3:
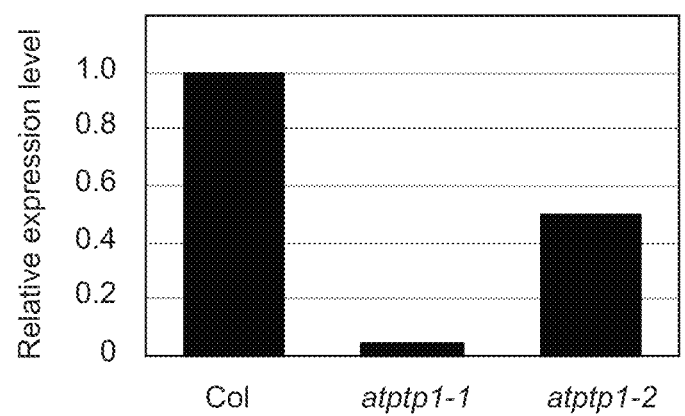
FIG. 3 is a characteristic diagram showing the results of calculating the relative expression levels of the At1g71860 gene measured by real-time PCR.

Each of the results were shown in terms of the relative expression level when the expression level in Col was designated as "1" after normalization of the expression level of the At1g71860 gene in each line with the expression level of 18S rRNA (FIG. 3). Based on differences compared with the expression level in Col, the atptp1-1 mutant was considered to be a knockout line, and the atptp1-2 mutant was considered to be a knockdown line.

(5) Salt Resistance Test for *Arabidopsis thaliana* Atptp1 Mutant

Seeds of the atptp1-1 mutant considered to be a knockout line and the atptp1-2 mutant considered to be a knockdown line in (4) above, and Col (non-recombinant wild-type) as a control were aseptically sowed on ½ MS agar media containing 0 mM, 125 mM, and 137.5 mM NaCl. They were cultivated for 21 days under conditions of 22° C. and 16 hours in the light/8 hours in the dark, and with a light intensity ranging from about 30 to 45 µE/cm² to perform a salt resistance test.

Figure 4:
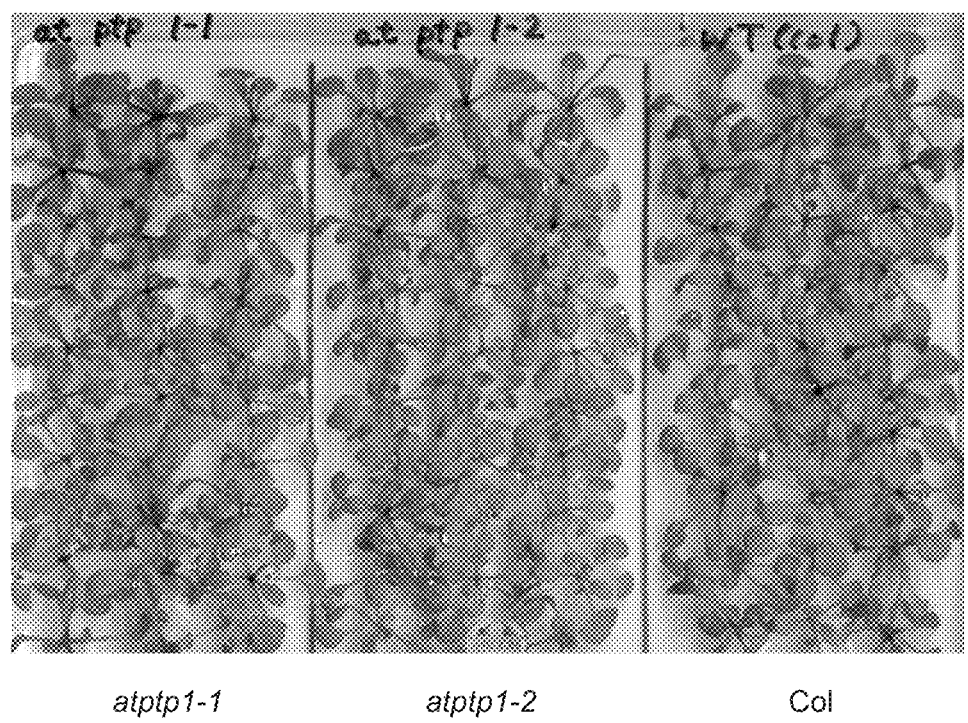
FIG. 4 shows photographs showing Col, atptp1-1 mutant, and atptp1-2 mutant sowed on ½ MS media (NaCl 0 mM) and then cultivated for 21 days.
Figure 5:
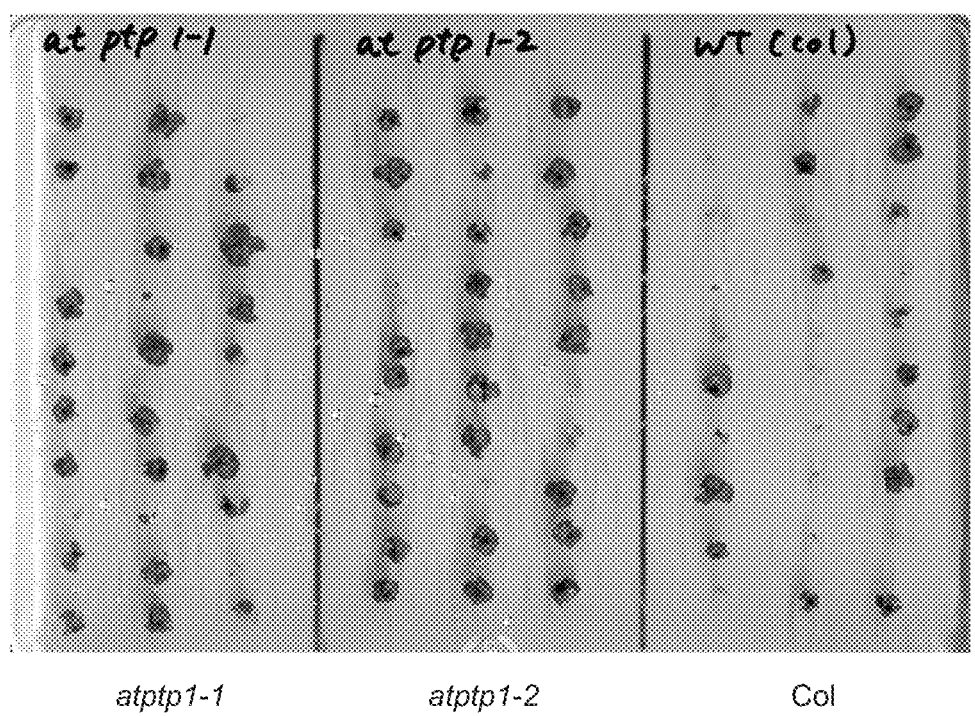
FIG. 5 shows photographs showing Col, atptp1-1 mutant, and atptp1-2 mutant sowed on ½ MS media (NaCl 125 mM) and then cultivated for 21 days.
Figure 6:
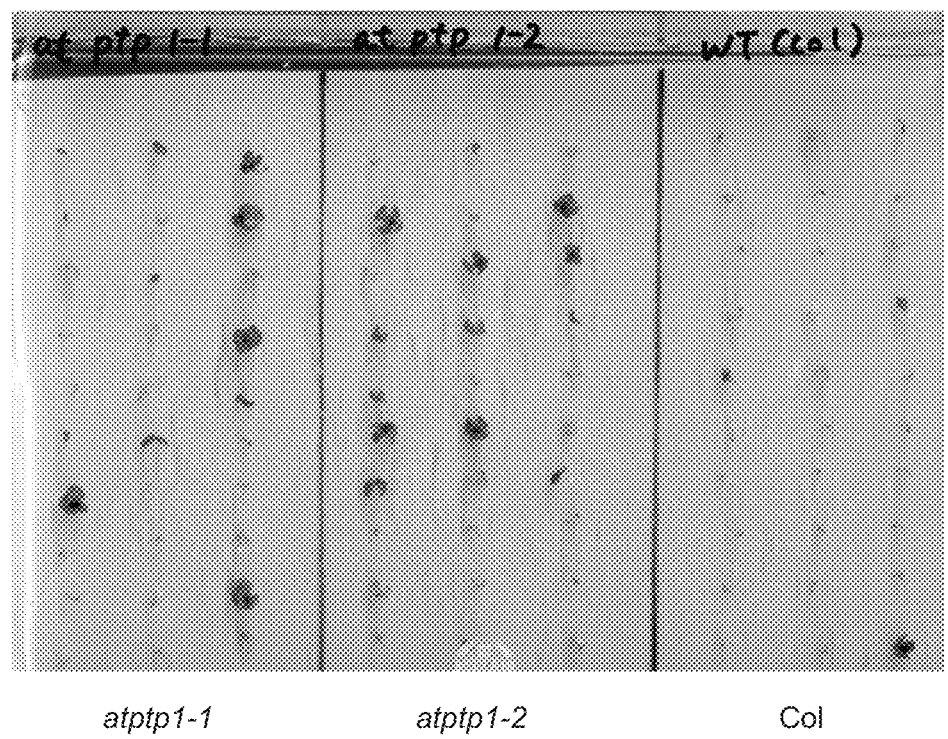
FIG. 6 shows photographs showing Col, atptp1-1 mutant, and atptp1-2 mutant sowed on ½ MS media (NaCl 137.5 mM) and then cultivated for 21 days.

FIGS. 4 to 6 show the salt resistance test results that are photographs of plates containing Col, atptp1-1 mutant and atptp1-2 mutant plants. FIGS. 5 and 6 revealed that the atptp1-1 mutant and atptp1-2 mutant plants exhibited more improved resistance to NaCl than Col.

As shown in the above results, a finding was obtained in this example such that resistance to high-salt concentrations can be imparted by suppressing the At1g71860 gene.

Example 2

In this example, plants overexpressing the At1g71860 gene and plants overexpressing a mutated At1g71860 gene were produced, and then examined for the possibility of growth under high-salt concentration conditions in a manner similar to that in Example 1. In addition, the mutated At1g71860 gene prepared in this example has an amino acid sequence prepared by substitution of the 175th cysteine in the amino acid sequence shown in SEQ ID NO: 2 with serine, and encodes tyrosine phosphatase having low sensitivity to oxidized glutathione and hydrogen peroxide.

(1) Plants Overexpressing the At1g71860 Gene

A nucleic acid fragment containing the At1g71860 gene was cloned from Col by the following procedure.

First, total RNA was collected from Col using an RNeasy Plant Mini Kit (Qiagen). After digestion of genomic DNA with DNase I (Invitrogen), cDNA was prepared from 5 µg of the total RNA using a StrataScript First Strand cDNA Synthesis System (Stratagene). PCR was performed using the cDNA as a template and primers, to which an Xba I or Sac I site had been added, 5'-TCTAGAATGGCGACCGG-TAAAACCTC-3' (SEQ ID NO: 12) and 5'-GAGCTCT-TAGGAACTCGTTCCAGCAT-3' (SEQ ID NO: 13). The nucleic acid fragment containing the cDNA of the At1g71860 gene was amplified by the PCR.

Next, the nucleic acid fragment amplified by PCR was cloned into the Xba I/Sac I site of a pGEM-T Easy vector (Promega). Furthermore, the resultant was substituted with γ-glucuronidase gene of a pBI121 binary vector, so that the full-length cDNA of the At1g71860 gene was expressed under the control of the cauliflower mosaic virus 35S promoter.

Next, the thus obtained construct was introduced into Col by an *Agrobacterium* method, thereby preparing overexpression plants. The thus obtained plants overexpressing the At1g71860 gene were named 35S-AtPTP1.

(2) Plants Overexpressing the Mutated At1g71860 gene

A nucleic acid fragment containing the mutated At1g71860 gene was prepared by PCR using the cDNA of the At1g71860 gene prepared in (1) above as a template. Specifically, in this PCR, a pair of primers that had been designed so as to substitute the 175$^{th}$ cysteine (TGC) of the protein encoded by the At1g71860 gene with serine (TCC), 5'-GACTGTTAAATCCGGGGACTATTTTCAA-3' (SEQ ID NO: 14) and 5'-AATAGTCCCCGGATTTAACAGTC-CTATT-3' (SEQ ID NO: 15), was used.

The cDNA of the mutated At1g71860 gene amplified by PCR was cloned into a pGEM-T Easy vector (Promega). Moreover, the resultant was substituted with a γ-glucuronidase gene of a pBI121 binary vector, so that the full-length cDNA of the mutated At1g71860 gene was expressed under the control of the cauliflower mosaic virus-derived 35S promoter.

Next, the thus obtained construct was introduced into Col by an *Agrobacterium* method, thereby producing overexpression plants. The thus obtained plants overexpressing the mutated At1g71860 gene were named 35S-AtPTP1 (C175S).

In addition, in tyrosine phosphatase encoded by the mutated At1g71860 gene, the 175$^{th}$ cysteine in the amino acid sequence shown in SEQ ID NO: 2 was substituted with serine. Regarding the substitution (mutation), as described in the Okayama Prefectural Technology Center for Agriculture, Forestry, and Fisheries, Research Institute for Biological Sciences, Annual Research Report 2007 (pp. 99-103), and Summaries of the 49$^{th}$ Annual Meeting, The Japanese Society of Plant Physiologists (p. 193 (3aD10)), the tyrosine phosphatase is known to maintain its activity under oxidizing conditions such as the presence of oxidized glutathione or hydrogen peroxide.

Figure 7:
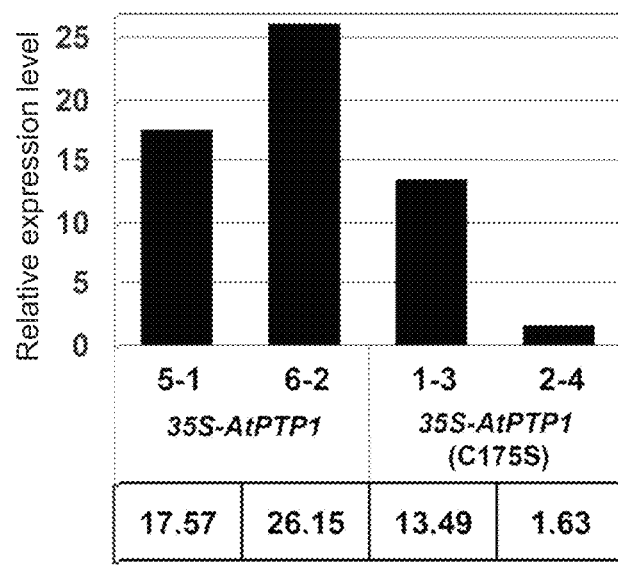
FIG. 7 is a characteristic diagram showing the results of calculating the relative expression levels of the At1g71860 gene and a mutated At1g71860 gene in overexpression plants produced in Example 2, as measured by real-time PCR.

(3) Comparison of the Expression Levels of the At1g71860 Gene in Overexpression Plants The expression level of the At1g71860 gene was measured by a real-time PCR method in a manner similar to that in Example 1 (4). The results are shown in FIG. 7. In addition, also in FIG. 7, the results were each shown in terms of relative expression level when the expression level in Col was designated as "1" after normalization of the expression level of the At1g71860 gene with the same of 18S rRNA. As shown in FIG. 7, both the overexpression plants produced in (1) above and the overexpression plants produced in (2) above were revealed to exhibit higher expression levels of the At1g71860 gene and the mutated At1g71860 gene than the expression level of the At1g71860 gene in wild-type plants.

In particular, overexpression plants 6-2 of the At1g71860 gene (produced in (1) above) were revealed to exhibit higher expression levels of the At1g71860 gene than that of overexpression plants 5-1. Moreover, overexpression plants 1-3 of the mutated At1g71860 gene (produced in (2) above) were revealed to exhibit higher expression levels of the mutated At1g71860 gene than that of overexpression plants 2-4. Furthermore, overexpression plants 1-3 and 2-4 of the At1g71860 gene (produced in (2) above) were revealed to exhibit lower expression levels of the At1g71860 gene than that of overexpression plants 5-1 and 6-2 (produced in (1) above).

(4) Salt Resistance Test for Each Overexpression Plant

Figure 8:
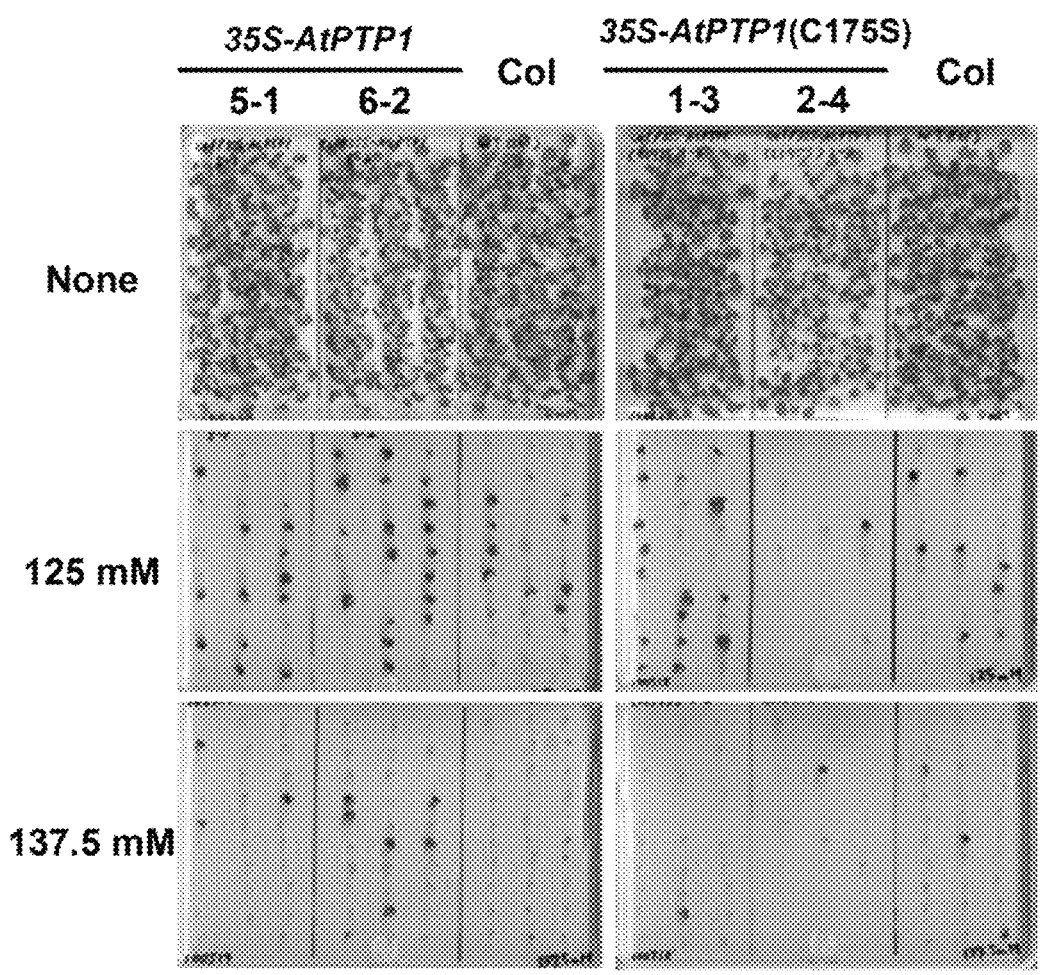
FIG. 8 shows photographs showing each overexpression plant (produced in Example 2) and Col sowed on ½ MS media (NaCl 0 mM, 125 mM, or 137.5 mM) and then cultivated for 21 days.

A salt resistance test was performed in a manner similar to that in Example 1 (5) using the overexpression plants produced in (1) above and the overexpression plants produced in (2) above. The salt resistance test results are shown in FIG. 8. The photographs on the left in FIG. 8 show plates containing the plants overexpressing the At1g71860 gene and wild-type *Arabidopsis thaliana* (Col) plants. Photographs on the right in FIG. 8 show plates containing the plants overexpressing the mutated At1g71860 gene and wild-type *Arabidopsis thaliana* (Col) plants.

As shown in FIG. 8, both the plants overexpressing the At1g71860 gene and the plants overexpressing the mutated At1g71860 gene were revealed to have more improved salt resistance than that of the wild-type *Arabidopsis thaliana* (Col). Also, as shown on the left in FIG. 8, overexpression plants 6-2 were revealed to have better salt resistance than that of overexpression plants 5-1. The result correlated with the degree of increase in expression level of the At1g71860 gene (FIG. 7), suggesting that better salt resistance could be acquired if the expression level of the At1g71860 gene is increased more significantly. Moreover, as shown on the right in FIG. 8, overexpression plants 1-3 were revealed to have better salt resistance than that of overexpression plants 2-4. The result correlated with the degree of increase in the expression level of the mutated At1g71860 gene (FIG. 7), suggesting that even better salt resistance could be obtained if the expression level of the mutated At1g71860 gene is significantly increased.

In addition, the expression level of the At1g71860 gene in the overexpression plants produced in (2) above was lower than that of the At1g71860 gene in the overexpression plants produced in (1) above, as shown in FIG. 7. In spite of the results, the overexpression plants produced in (2) above exhibited salt resistance equivalent to that of the overexpression plants produced in (1) above, as shown in FIG. 8. The results revealed that the overexpression of the At1g71860 gene, in which a mutation had been introduced to maintain the activity under oxidizing conditions, is preferred to impart salt resistance to plants.

All publications, patents, and patent applications cited herein are incorporated herein by reference in their entirety.

The invention claimed is:

1. A method for increasing the resistance of a plant to high salt concentration, comprising:
   altering, in a plant, the level of expression of a protein tyrosine phosphatase enzyme which comprises an amino acid sequence having at least 90% amino acid identity to the amino acid sequence of SEQ ID NO: 2; and
   evaluating the salt-resistance of the plant.

2. The method according to claim 1, wherein said altering comprises decreasing the level of expression of said protein.

3. The method according to claim 1, wherein said altering comprises increasing the level of expression of said protein.

4. The method according to claim 1, wherein said protein comprises the amino acid sequence of SEQ ID NO: 2 but in which 1-20 amino acids have been deleted, substituted and/or added in the sequence of SEQ ID NO: 2.

5. The method according to claim 1, wherein said altering comprises introducing, into said plant, a polynucleotide encoding a protein tyrosine phosphatase enzyme comprising an amino acid sequence having at least 90% amino acid identity to the amino acid sequence of SEQ ID NO: 2,
   and wherein said protein comprises a mutation that allows it to maintain phosphatase activity under oxidizing conditions.

6. A method for producing a plant having increased resistance to high salt concentration as compared to a wild-type plant, comprising the steps of:
   altering, in a plant, the level of expression of a protein tyrosine phosphatase enzyme which comprises an amino acid sequence having at least 90% amino acid identity to the amino acid sequence of SEQ ID NO: 2; and
   evaluating the salt-resistance of the plant, and then selecting a line having significantly improved resistance to high salt concentration.

7. The method according to claim 6, wherein said altering comprises decreasing the level of expression of said protein.

8. The method according to claim 6, wherein said altering comprises increasing the level of expression of said protein.

9. The method according to claim 6, wherein said protein comprises the amino acid sequence of SEQ ID NO: 2 but in which 1-20 amino acids have been deleted, substituted and/or added in the sequence of SEQ ID NO: 2.

10. The method according to claim 6, wherein said altering comprises introducing, into said plant, a polynucleotide encoding a protein tyrosine phosphatase enzyme comprising an amino acid sequence having at least 90% amino acid identity to the amino acid sequence of SEQ ID NO: 2,
    and wherein said protein comprises a mutation that allows it to maintain phosphatase activity under oxidizing conditions.

11. The method according to claim 5, wherein said mutation is the substitution of cysteine, at a position corresponding to position 175 in SEQ ID NO: 2, with a different amino acid.

12. The method according to claim 10, wherein said mutation is the substitution of cysteine, at a position corresponding to position 175 in SEQ ID NO: 2, with a different amino acid.

13. The method according to claim 2, wherein the level of expression of said protein is less than 0.5-times compared with the wild type.

14. The method according to claim 3, wherein the level of expression of said protein is more than 17-times compared with the wild type.

15. The method according to claim 5, wherein the level of expression of said protein is more than 13-times compared with the wild type.

16. The method according to claim 7, wherein the level of expression of said protein is less than 0.5-times compared with the wild type.

17. The method according to claim 8, wherein the level of expression of said protein is more than 17-times compared with the wild type.

18. The method according to claim 10, wherein the level of expression of said protein is more than 13-times compared with the wild type.

* * * * *